United States Patent [19]
Visconti

[11] Patent Number: 5,743,883
[45] Date of Patent: Apr. 28, 1998

[54] THORACENTESIS CATHETER INSTRUMENTS HAVING SELF-SEALING VALVES

[76] Inventor: Peter L. Visconti, 1453 W. Rosemont Ave., Chicago, Ill. 60660

[21] Appl. No.: 476,690

[22] Filed: Jun. 7, 1995

[51] Int. Cl.⁶ .................................................. A61M 5/178
[52] U.S. Cl. .................. 604/169; 604/167; 604/256; 604/264; 251/149.1
[58] Field of Search ............................ 604/167, 169, 604/247, 256, 264, 236, 905, 93, 249, 278, 283; 251/149.1, 149.8, 129.02

[56] References Cited

U.S. PATENT DOCUMENTS

| | | |
|---|---|---|
| 1,087,845 | 2/1914 | Stevens . |
| 1,103,967 | 7/1914 | Hughes . |
| 1,527,291 | 2/1925 | Zorraquin . |
| 1,867,624 | 7/1932 | Hoffman . |
| 2,485,842 | 10/1949 | Pennington . |
| 2,614,764 | 10/1952 | Annicq . |
| 2,623,521 | 12/1952 | Shaw . |
| 2,627,388 | 2/1953 | Johnson et al. . |
| 2,630,803 | 3/1953 | Baran . |
| 2,842,124 | 7/1958 | James . |
| 2,844,333 | 7/1958 | Davidson . |
| 3,157,201 | 11/1964 | Littmann . |
| 3,276,472 | 10/1966 | Jinkens et al. . |
| 3,313,299 | 4/1967 | Spademan . |
| 3,459,183 | 8/1969 | Ring et al. . |
| 3,459,188 | 8/1969 | Roberts . |
| 3,477,437 | 11/1969 | Goldberg . |
| 3,530,492 | 9/1970 | Ferber . |
| 3,542,026 | 11/1970 | Bledsoe . |
| 3,547,119 | 12/1970 | Hill et al. . |
| 3,557,778 | 1/1971 | Hughes ................... 604/236 |
| 3,703,899 | 11/1972 | Calinog . |
| 3,713,447 | 1/1973 | Adair . |
| 3,727,613 | 4/1973 | Sorenson et al. . |
| 3,765,420 | 10/1973 | Felczak . |
| 3,774,604 | 11/1973 | Danielsson . |
| 3,830,225 | 8/1974 | Shinnick . |
| 3,834,372 | 9/1974 | Turney . |
| 3,840,008 | 10/1974 | Noiles . |
| 3,853,127 | 12/1974 | Spademan . |
| 3,875,938 | 4/1975 | Mellor . |
| 3,895,632 | 7/1975 | Plowiecki . |

(List continued on next page.)

FOREIGN PATENT DOCUMENTS

| | | |
|---|---|---|
| 405883 A3 | 1/1991 | European Pat. Off. . |
| 232600 B1 | 4/1991 | European Pat. Off. . |
| 575559 | 3/1923 | France . |
| 7535678 | 4/1975 | France . |
| 897224 | 4/1982 | U.S.S.R. . |
| WO 94/06506 | 3/1994 | WIPO . |

OTHER PUBLICATIONS

"Custom Engineered Precision Rubber Components", Vernay Laboratories, Inc., dated unknown, 10 pages.

Mark A. Talamini, MD and Thomas R. Gadacz, MD, "Laparoscopic Equipment and Instrumentation", Surgical Laparoscopy, 1991, pp. 23, 40–41.

"The Argyle® Turkel™ Safety Thoracentesis System" Product Literature, Sherwood Medical Company, 1993, 7 pages, particularly p. 3.

Col. Douglas W. Jenkins, Jr., MC, USAFR; Capt. Michael K. McKinney, MC, USAF; Michael W. Szpak, MD and Jasper L. Booker, Jr., MD "Veres Needle in the Pleural Space", Southern Medical Journal, vol. 76, No. 11, Nov., 1983, pp. 1383–1385.

Primary Examiner—Robert A. Hafer
Assistant Examiner—Justine R. Yu
Attorney, Agent, or Firm—Hill & Simpson

[57] ABSTRACT

The present invention provides thoracentesis catheter instruments having self-sealing valves utilized in invasive medical procedures. The thoracentesis instruments provide automatic sealing of a flow path by the self-sealing valve upon removal of a needle from a catheter. A drainage flow path to a pleural cavity is established by manual movement of another valve. The self-sealing valve prevents insertion of the needle through the valve and the catheter.

31 Claims, 4 Drawing Sheets

U.S. PATENT DOCUMENTS

| | | |
|---|---|---|
| 3,934,576 | 1/1976 | Danielsson . |
| 3,952,729 | 4/1976 | Libman et al. . |
| 3,977,400 | 8/1976 | Moorehead . |
| 3,990,472 | 11/1976 | Etes ........................................... 604/247 |
| 3,994,287 | 11/1976 | Turp et al. . |
| 4,000,739 | 1/1977 | Stevens . |
| 4,073,297 | 2/1978 | Kopp . |
| 4,099,528 | 7/1978 | Sorenson et al. . |
| 4,177,814 | 12/1979 | Knepshield et al. . |
| 4,233,982 | 11/1980 | Bauer et al. . |
| 4,245,635 | 1/1981 | Kontos . |
| 4,252,122 | 2/1981 | Halvorsen . |
| 4,261,357 | 4/1981 | Kontos ........................................... 604/167 |
| 4,308,875 | 1/1982 | Young . |
| 4,311,136 | 1/1982 | Weikl et al. . |
| 4,314,565 | 2/1982 | Lee . |
| 4,379,458 | 4/1983 | Bauer et al. ............................. 604/264 |
| 4,403,617 | 9/1983 | Tretinyak . |
| 4,447,235 | 5/1984 | Clarke . |
| 4,496,348 | 1/1985 | Genese et al. . |
| 4,531,935 | 7/1985 | Berryessa . |
| 4,535,773 | 8/1985 | Yoon . |
| 4,535,819 | 8/1985 | Atkinson et al. ........................ 604/247 |
| 4,540,411 | 9/1985 | Bodicky . |
| 4,566,480 | 1/1986 | Parham . |
| 4,626,245 | 12/1986 | Weinstein . |
| 4,627,841 | 12/1986 | Dorr . |
| 4,653,475 | 3/1987 | Seike et al. . |
| 4,655,226 | 4/1987 | Lee . |
| 4,655,752 | 4/1987 | Honkanen et al. .................... 604/256 |
| 4,700,694 | 10/1987 | Shishido . |
| 4,735,215 | 4/1988 | Goto et al. . |
| 4,745,950 | 5/1988 | Mathieu . |
| 4,784,156 | 11/1988 | Garg . |
| 4,808,168 | 2/1989 | Warring . |
| 4,832,044 | 5/1989 | Garg . |
| 4,840,184 | 6/1989 | Garg . |
| 4,842,591 | 6/1989 | Luther ...................................... 604/283 |
| 4,844,087 | 7/1989 | Garg . |
| 4,850,373 | 7/1989 | Zadloukal et al. . |
| 4,850,973 | 7/1989 | Jordan et al. . |
| 4,869,717 | 9/1989 | Adair . |
| 4,887,998 | 12/1989 | Martin et al. . |
| 4,891,044 | 1/1990 | Mitchell . |
| 4,902,280 | 2/1990 | Lander . |
| 4,907,599 | 3/1990 | Taylor . |
| 4,917,668 | 4/1990 | Haindl ..................................... 604/169 |
| 4,931,042 | 6/1990 | Holmes et al. . |
| 4,973,312 | 11/1990 | Andrew . |
| 5,030,199 | 7/1991 | Barwick et al. ......................... 604/93 |
| 5,036,860 | 8/1991 | Leigh et al. . |
| 5,057,084 | 10/1991 | Ensminger et al. . |
| 5,059,180 | 10/1991 | McLees . |
| 5,078,688 | 1/1992 | Lobodzinski et al. . |
| 5,098,388 | 3/1992 | Kulhashi et al. . |
| 5,098,394 | 3/1992 | Luther . |
| 5,100,377 | 3/1992 | Freitas et al. ........................... 604/236 |
| 5,104,381 | 4/1992 | Gresl et al. . |
| 5,108,380 | 4/1992 | Herlitze et al. . |
| 5,122,122 | 6/1992 | Allgood . |
| 5,139,485 | 8/1992 | Smith et al. . |
| 5,154,701 | 10/1992 | Cheer et al. . |
| 5,195,980 | 3/1993 | Catlin ...................................... 604/167 |
| 5,226,879 | 7/1993 | Ensminger et al. .................... 604/167 |
| 5,300,046 | 4/1994 | Scarfone et al. ........................ 604/256 |
| 5,350,360 | 9/1994 | Ensminger et al. ..................... 604/93 |
| 5,372,306 | 12/1994 | Yianilos ................................. 251/149.1 |
| 5,383,259 | 1/1995 | McIntire ................................... 24/300 |
| 5,441,487 | 8/1995 | Vedder ..................................... 604/169 |
| 5,542,923 | 8/1996 | Ensminger et al. ..................... 604/93 |

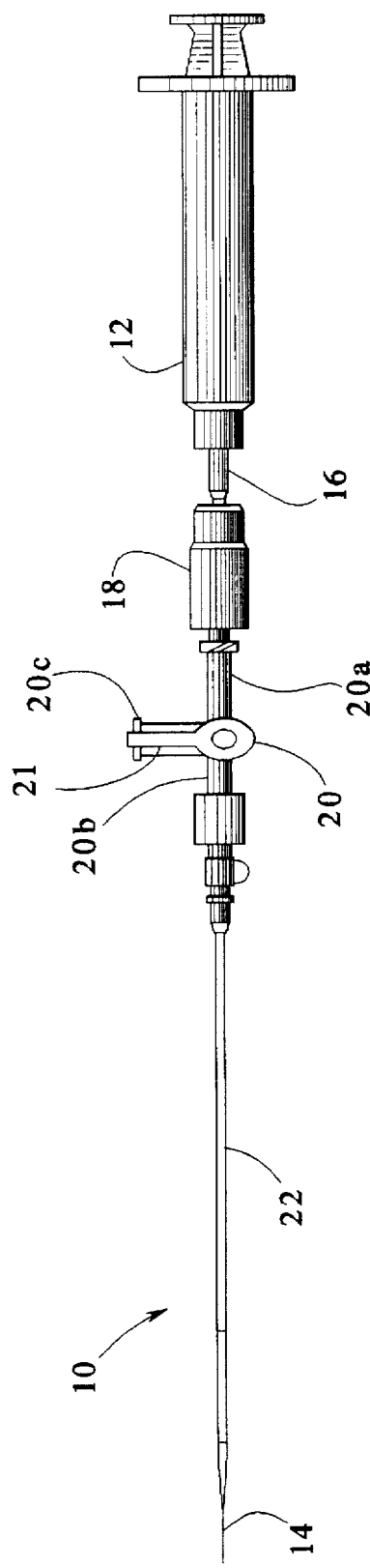
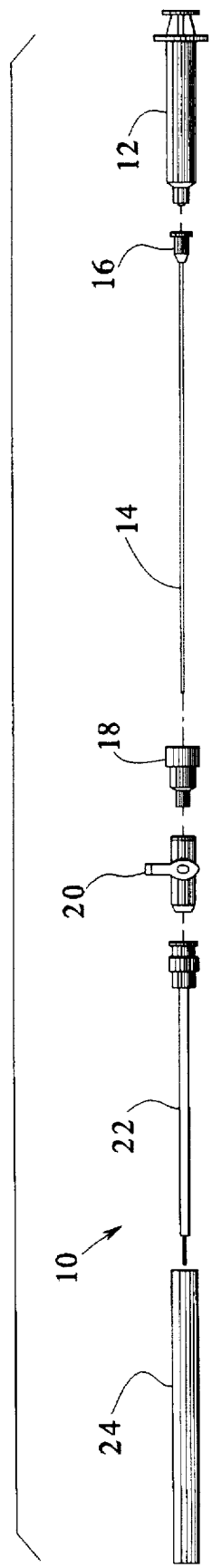
FIG. 1
FIG. 2

THORACENTESIS CATHETER INSTRUMENTS HAVING SELF-SEALING VALVES

FIELD OF THE INVENTION

This invention generally relates to medical instruments. More specifically, this invention relates to thoracentesis catheter instruments having self-sealing valves utilized in invasive medical procedures.

BACKGROUND OF THE INVENTION

A thoracentesis procedure is a medical procedure for removing or draining fluid from the pleural cavity. The thoracentesis procedure includes inserting a thoracentesis device into the pleural cavity of a patient and creating a drainage path from the pleural cavity out of the patient.

Typically, a needle is utilized to insert a catheter into the pleural cavity. The needle is withdrawn and the catheter remains in the pleural cavity creating a drainage path out of the cavity. Vacuum air pressure is applied to the drainage path through the catheter to remove fluid from the pleural cavity. While performing a thoracentesis procedure it is important to maintain a negative pressure or vacuum on the thoracentesis device to prevent the lungs from collapsing.

Existing thoracentesis devices have exhibited drawbacks. For example, existing devices have created a flow path to the pleural cavity immediately upon withdrawal of the needle. If a negative pressure is not present or not maintained on the flow path a risk of lung collapse exists. Existing devices have included a valve to close the drainage path. However, if the valve fails, a flow path through the failed valve is open to the pleural cavity. Also, maintaining a sterile thoracentesis instrument and preventing reuse of the instrument are important safety objectives.

Therefore, needs exist to improve medical devices. Particularly, needs exist to improve thoracentesis catheter instruments utilized in invasive medical procedures. The present invention satisfies these and other needs to improve thoracentesis instruments.

Other aspects and advantages of the present invention will become apparent after reading this disclosure, including the claims, and reviewing the accompanying drawings.

SUMMARY OF THE INVENTION

The present invention provides thoracentesis catheter instruments having self-sealing valves utilized in invasive medical procedures. The thoracentesis instruments provide automatic sealing of a flow path by the self-sealing valve upon removal of a needle from a catheter. A drainage flow path to a pleural cavity is established by manual movement of another valve.

After withdrawal of a needle, the self-sealing valve prevents insertion of the needle through the valve and the catheter. More particularly, a plunger in the valve prevents insertion of the needle and prevents the needle from contacting a sealing ball. Prior to withdrawal of the needle, the plunger holds itself in an un-fired position such that there is no biasing force applied to the sealing ball. The plunger also includes a slanted surface that guides the ball to a ball seat to seal the valve.

BRIEF DESCRIPTION OF THE DRAWINGS

FIG. 1 is an elevational view of a thoracentesis catheter instrument made in accordance with the principles of the present invention.

FIG. 2 is an exploded view of the thoracentesis catheter instrument of FIG. 1.

DETAILED DESCRIPTION OF THE INVENTION

Figure 3:
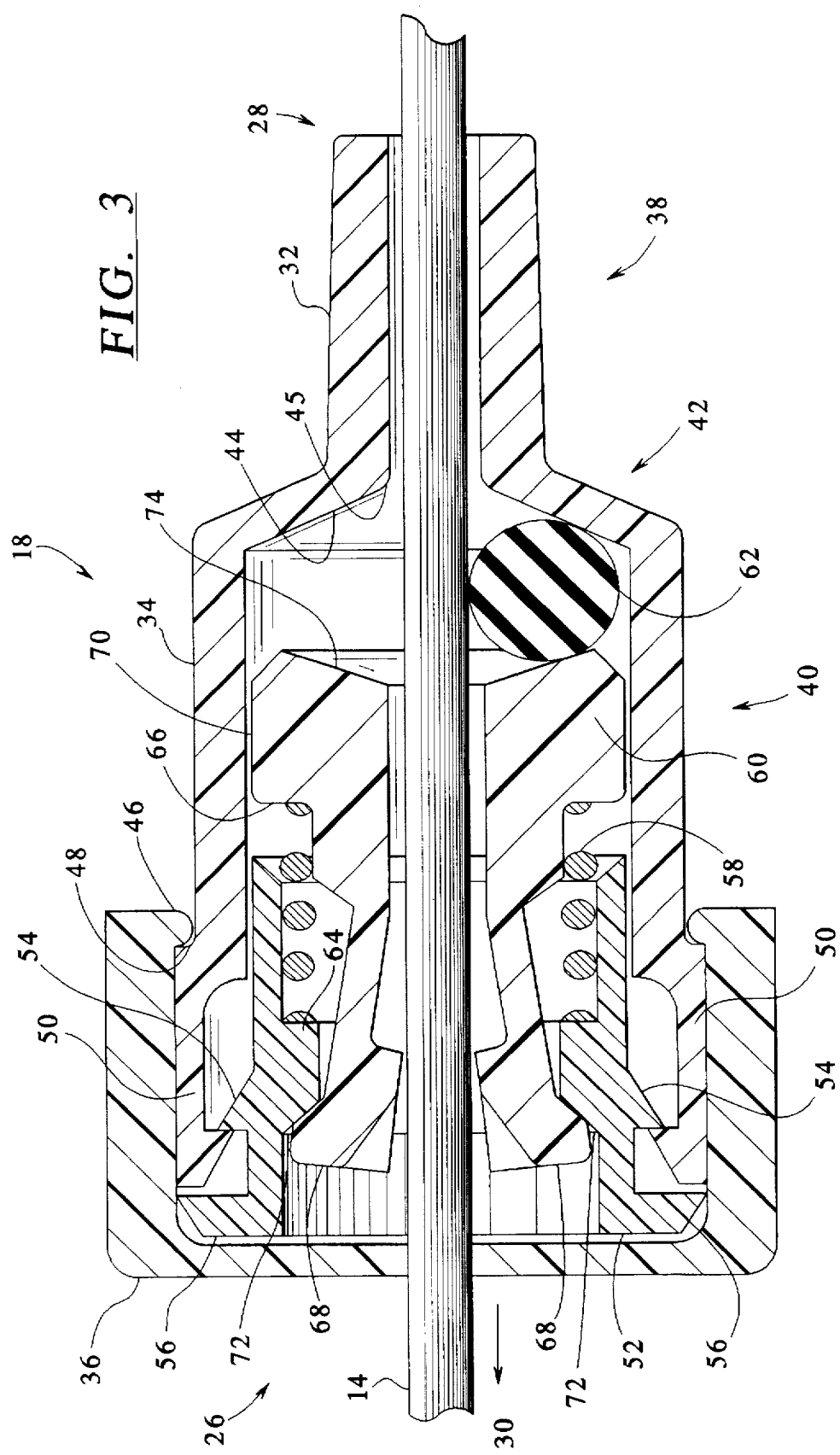
FIG. 3 is a cross-sectional view of a self-sealing valve made in accordance with the principles of the present invention.

Although the present invention can be made in many different forms, the preferred embodiments are described in this disclosure and shown in the attached drawings. This disclosure exemplifies the principles of the present invention and does not limit the broad aspects of the invention only to the illustrated embodiments.

FIG. 1 shows an elevational view of a thoracentesis catheter instrument 10 made in accordance with the principles of the present invention and FIG. 2 shows an exploded view of the thoracentesis catheter instrument 10. The thoracentesis catheter instrument 10 includes a syringe 12 removably connected to an elongated needle 14 by a luer fitting 16. The luer fitting 16 is permanently attached to the needle 14. Preferably, the needle 14 is a hollow needle. The thoracentesis catheter instrument 10 also includes a self-sealing valve 18, a stopcock valve 20, a catheter 22, and a protective catheter sheath 24. The protective sheath 24 is shown in FIG. 2. The thoracentesis catheter instrument can also be utilized as a paracentesis device.

The needle 14 extends from the syringe 12 through the self-sealing valve 18, through the stopcock valve 20, and through the catheter 22. There are interference slip fits or luer fittings between the self-sealing valve 18 and the stopcock valve 20 and between the stopcock valve 20 and the catheter 22. The removable catheter sheath 24 protects the needle 14 and the catheter 22 when the instrument 10 is not in use.

The self-sealing valve 18 is fitted to a manual stopcock valve 20. The stopcock valve 20 has three ports (a self-sealing valve port 20a, a catheter port 20b, and a drainage port 20c) and an external lever 21. The external lever 21 is manually positioned to three separate alternative positions in which each position connects two selected ports by a passageway.

In a first stopcock position, the lever 21 is aligned with the drainage port 20c and the self-sealing valve port 20a is connected to the catheter port 20b by a passageway; while, the drainage port 20c is closed. This first position is required for the needle 14 to pass through the stopcock valve 20 as shown in FIG. 1 because the needle extends through the passageway between the catheter port 20b and the self-sealing valve port 20a. The needle 14 prevents the lever 21 from being repositioned when the needle extends through the stopcock valve 20. The thoracentesis instrument 10 is also in this position immediately upon removal of the needle 14 from the device. Also, the self-sealing valve 18 automatically closes upon removal of the needle 14.

After removal of the needle 14 from the thoracentesis instrument 10, the stopcock valve lever 21 must be manually positioned to a second position to provide a drainage path from a patient. In the second position, the lever 21 is aligned with the catheter port 20b. In the second position, the catheter port 20b and the drainage port 20c are connected by a passageway; while, the self-sealing valve port 20a is closed.

The lever 21 can also be manually moved to a third position after the needle 14 has been removed. The lever 21 is aligned with the self-sealing valve port 20a when the lever 21 is in the third position. In the third position, the self-sealing valve port 20a is connected to the drainage port 20c by a passageway; while, the catheter port 20b is closed.

FIG. 3 shows a cross-sectional view of one embodiment of a self-sealing valve 18 made in accordance with the principles of the present invention. The self-sealing valve 18 is shown in FIG. 3 in an un-fired position, in which the needle 14 extends through the valve 18. The self-sealing valve 18 has a syringe end 26 facing the syringe 12 and a catheter end 28 facing the catheter 22. The needle 14 is withdrawn from the self-sealing valve 18 out of the syringe end 26 in the direction of arrow 30 as described below. A luer fitting 32 is provided at the catheter end 28 for connection to the stop-cock valve 20.

The self-sealing valve 18 includes a housing having a front housing 34 snap-fitted to a back housing 52. An end cap 36 covers the back housing 52 and has an opening for the needle 14. The front housing 34 has a first annular section 38 connected to a second annular section 40 by a transition section 42. The first annular section 38 defines a passageway having an inner diameter larger than the outer diameter of the needle 14. The transition section 42 extends from the first annular section 38 radially outward to the second annular section 40 such that the second annular section 40 has a larger inner diameter than the first annular section 38. The transition section 42 is positioned at angle relative to a reference plane perpendicular to a longitudinal needle axis and thus, defines an annular slanted housing surface 44. The annular slanted housing surface 44 defines a ball seat 45 at an opening to the passageway through the first annular section 38. The front housing 34 also includes a locking member 50, preferably two spaced apart locking members 50, which form part of the second annular section 40.

The front housing 34 is removably locked or snap-fitted to the back housing 52 by locking members 50. The locking members 50 engage an annular locking tab 54 on the back housing 52. The locking members 50 are flexible to spread apart radially to slip over the locking tab 54 to lock onto the back housing 52 when the valve 18 is assembled. The locking members 50 can also be flexed radially outward to disengage the locking tab 54 to disassemble the valve 18. An annular ledge 56 on the back housing 52 is positioned adjacent the locking members 50 to also secure the back housing 52 to the front housing 34.

The end cap 36 is made from a flexible material and stretches over the front housing 34 to grip onto the front housing 34. An annular projection 46 on the end cap 36 may also be provided to grip onto an annular ledge 48 on the front housing 34.

The self-sealing valve 18 also includes a spring 58, a plunger 60, and a ball 62 which are contained within the valve housing. One end of the spring 58 abuts a spring seat 64 on the back housing 52 and the other spring end abuts a spring seat 66 on the plunger 60. Accordingly, the spring 58 biases the plunger 60 toward the catheter end 28 of the valve 18.

The plunger 60 has two beams 68 extending from a plunger head 70. The beams 68 are outwardly flexible to engage and disengage an annular ledge 72 on the back housing 52. When the valve 18 is in the un-fired position with the needle 14 extending through the valve 18 as shown in FIG. 3, the beams 68 are spread outward by the needle 14 and engage the annular ledge 72. The needle 14 spreads the beams 68 apart causing an interference between the plunger 60 and the back housing 52 such that the plunger 60 is held in place against the spring force. In this manner, the beams 68 hold the plunger 60 in an un-fired position against the biasing force of the spring 58. Preferably, the annular ledge 72 defines a slanted surface angled inwardly and toward the catheter end 28 which engages a corresponding slanted surface on the beams 68. The plunger head 70 has a conical shaped annular slanted plunger surface 74 which guides the ball 62 toward the ball seat 45 when the needle 14 is removed from the valve 18.

When the needle 14 extends through the self-sealing valve 18, the plunger 60 is not biased against the ball 62 because the beams 68 hold the plunger 60 in place. Because there is no biasing force on the ball 62 when the valve 18 is in the un-fired mode, the ball 62 can be made from relatively soft materials that might otherwise deform under a biasing force. Accordingly, the ball 62 could be made from soft plastic materials or harder materials, such as stainless steel if desired.

Figure 4:
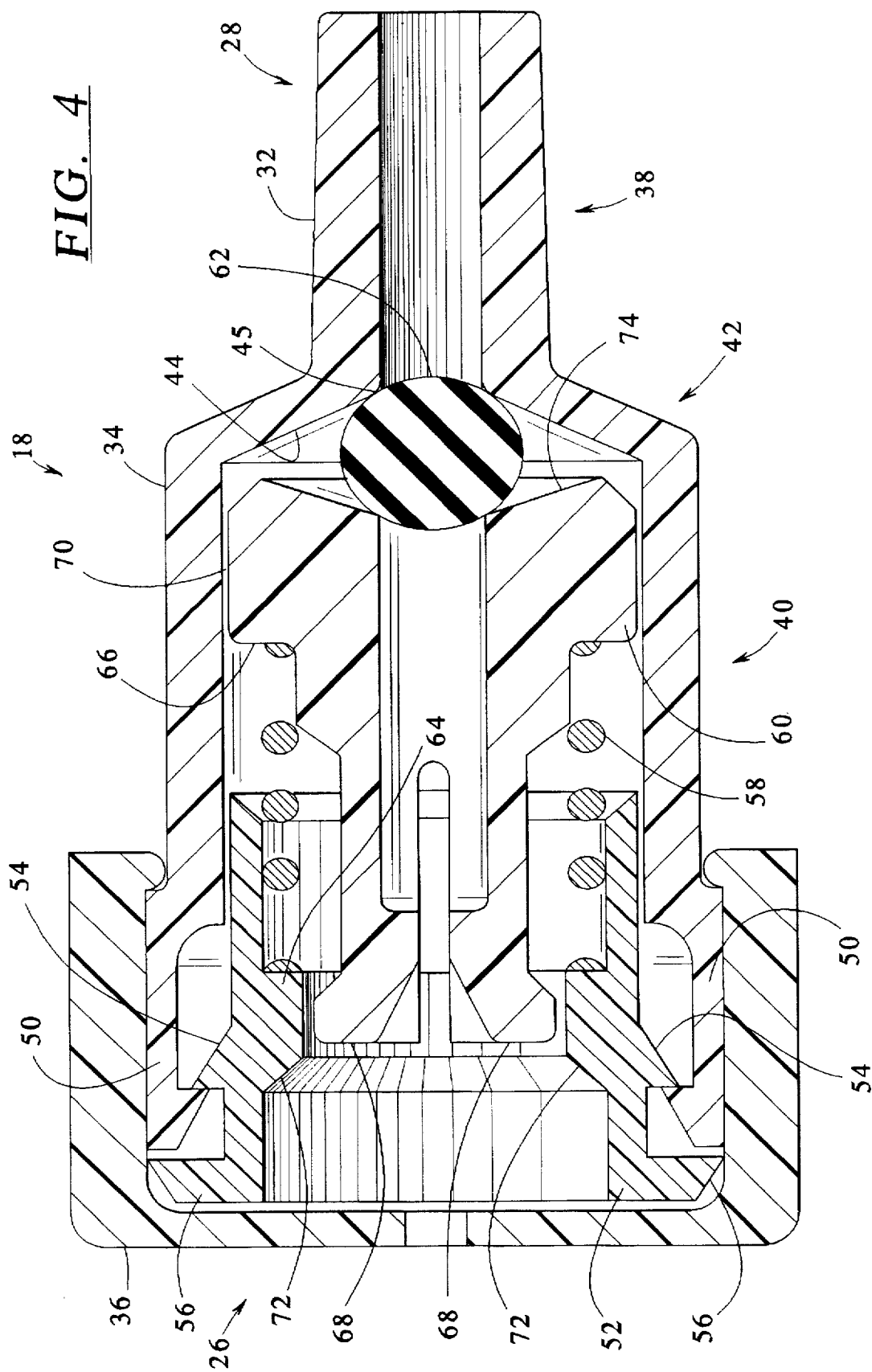
FIG. 4 is a cross-sectional view of the self-sealing valve of FIG. 3 in a closed valve mode.

FIG. 4 shows a cross-sectional view of the self-sealing valve 18 in a fired or closed valve mode after the needle 14 has been removed from the valve 18. With the needle 14 withdrawn out of the syringe end 26, the beams 68 move radially inward and disengage from the annular ledge 72. The spring 58 moves the plunger forward toward the catheter end 28. The plunger 60 contacts the ball 62 and biases the ball 62 into sealing engagement with the ball seat 45. The diameter of the ball is sufficiently larger than the diameter of the passageway through the first annular section 38 to enable the ball 62 to seal the passageway. The seal between the ball 62 and the ball seat 45 is an air and fluid tight seal. The annular slanted plunger surface 74 guides the ball 62 along the annular slanted housing surface 44 toward the ball seat 45. The annular slanted plunger surface 74 also improves the seal because the surface 74 maintains the ball 62 in a centered orientation on the ball seat 45.

After the self-sealing valve 18 is fired, the needle 14 cannot be reinserted through the valve 18. Specifically, in the fired mode, the back housing 52 constrains the beams 68 from spreading outward. The beams 68 are positioned close to each other such that there is insufficient space for the needle 14 to pass between the beams 68. Thus, if an attempt is made to insert the needle 14 into the valve 18, the needle 14 will be prevented from insertion by the beams 68. The needle 14 is prevented from contacting the ball 62 during an attempted needle insertion. This prevents the needle from damaging the ball 62 and compromising the seal.

Figure 5:
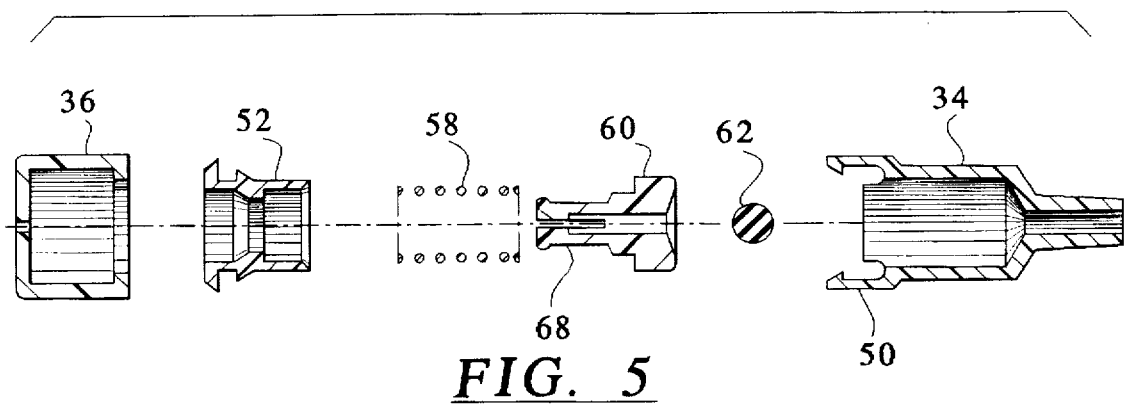
FIG. 5 is an exploded view of the self-sealing valve of FIG. 3.

FIG. 5 shows an exploded cross-sectional view of the components of the self-sealing valve 18 as described in the disclosure.

Figure 6:
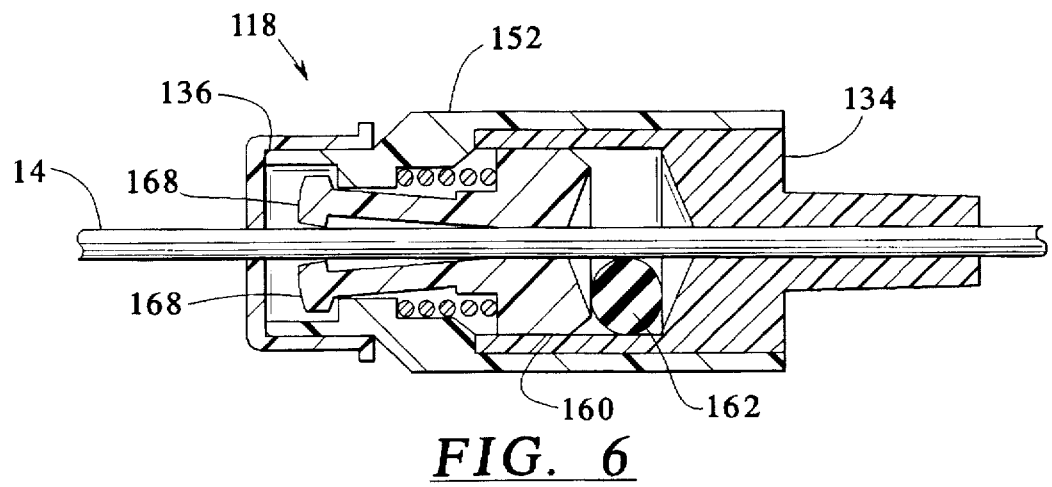
FIG. 6 is a cross-sectional view of another embodiment of a self-sealing valve made in accordance with the principles of the present invention.
Figure 7:
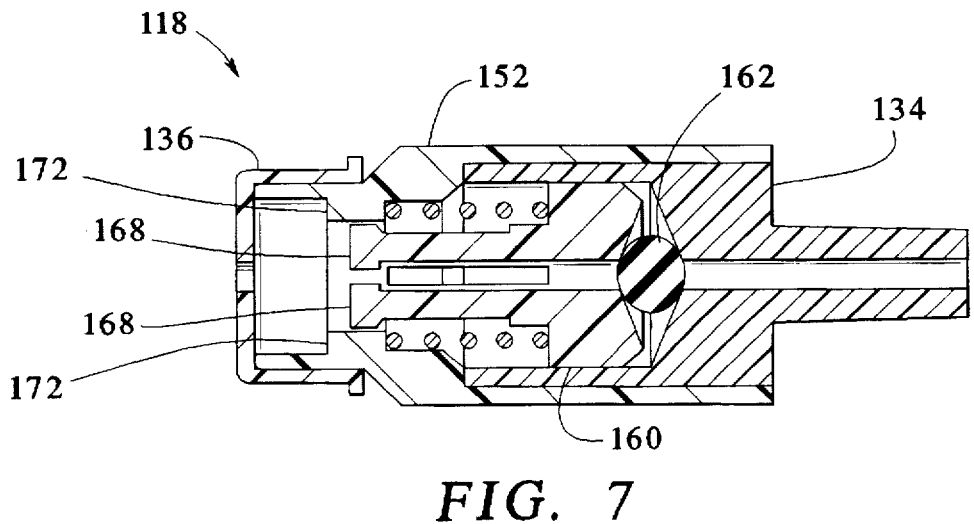
FIG. 7 is a cross-sectional view of the self-sealing valve of FIG. 6 in a closed valve mode.

FIGS. 6 and 7 show cross-sectional views of another embodiment of a self-sealing valve 118 made in accordance with the principles of the present invention. FIG. 6 shows the valve 118 in an un-fired mode with the needle 14 extending through the valve 118. FIG. 7 shows the valve 118 in a fired mode with the needle 14 removed from the valve 118. The valve 118 includes a housing having a front housing 134 bonded to a back housing 152. An end cap 136 stretches over the back housing 152 to grip onto the back housing 152. The back housing 152 includes an annular ledge 172 which is engaged and disengaged by the beams 168 of the plunger 160. The annular ledge 172 is shown as being perpendicular to the needle axis.

Operation of the thoracentesis catheter instrument 10 will be described with initial reference to FIG. 1. The catheter sheath 24 is removed and the instrument is inserted into a patient at a desired location. The needle 14 is removed by pulling the syringe 12 away from the self-sealing valve 18.

Referring to FIGS. 3 and 4, the self-sealing valve 18 is automatically placed in a fired mode. When the needle 14 is removed from the self-sealing valve 18, the self-sealing valve 18 closes automatically. More specifically, as the tip of the needle 14 is withdrawn past the beams 68 of the plunger 60, the beams 68 disengage the annular ledge 72 and the spring 58 moves the plunger 60 forward. The annular slanted plunger surface 74 contacts the ball 62 and the ball 62 travels along the slanted surfaces 44, 74 until the ball 62 rests on the ball seat 45 to seal the passageway. The spring 58 maintains a biasing force on the plunger 60 and on the ball 62 to maintain the seal.

At this stage, the drainage path from the patient through the catheter 22 and through the stopcock valve 20 remains closed. Referring to FIG. 1, the stopcock lever 21 is moved from the closed drainage path position to an open drainage path position, i.e., from the first position to the second position, respectively, as described above. Accordingly, a drainage passageway from the patient is not established until the needle 14 is removed and the stopcock valve 20 is manually positioned to connect the catheter port 20b to the drainage port 20c.

While the preferred embodiments have been illustrated and described, numerous changes and modifications can be made without significantly departing from the spirit and scope of this invention. Therefore, the inventor intends that such changes and modifications be covered by the appended claims.

What is claimed is:

1. A valve for use in a thoracentesis device, the valve comprising:
    a housing having a first end and defining an opening through the first end;
    a plunger movable within the housing from a first plunger position to a second plunger position, the plunger having a plunger portion movable from a first portion position engaged with a catch inside the housing such that the plunger is maintained in the first plunger position to a second portion position which permits the plunger to move to the second plunger position;
    a biasing member adjacent the plunger, wherein the biasing member biases the plunger toward the first end; and,
    a seal in sealing engagement with the opening when the plunger is in the second plunger position.

2. The valve of claim 1 wherein the valve is adapted to have a needle extend through the valve such that the needle contacts the plunger portion when the plunger portion is in the first portion position.

3. The valve of claim 2 wherein the plunger portion moves from the first plunger position to the second plunger position when the needle is removed from the valve.

4. The valve of claim 2 wherein the plunger portion prevents the needle from extending through the valve when the plunger is in the second plunger position.

5. The valve of claim 1 wherein the valve defines an axis through the valve, and wherein the plunger portion is flexible in a radial direction to engage a first surface on the housing when the plunger portion is in the first portion position and disengage the first surface when the plunger portion is in the second portion position.

6. The valve of claim 5 wherein the plunger further comprises a plunger head connected to the plunger portion, and wherein the plunger portion comprises at least one beam extending axially from the plunger head.

7. The valve of claim 6 wherein the beam comprises a slanted surface that engages the first surface on the housing when the beam is in the first plunger position.

8. The valve of claim 5 wherein the first surface defines a reference plane perpendicular to the axis.

9. The valve of claim 5 wherein the first surface is slanted at an angle relative to the axis.

10. The valve of claim 1 wherein the plunger further comprises a plunger head connected to the plunger portion, the plunger head contacting the seal when the plunger is in the second plunger position.

11. The valve of claim 10 wherein the plunger has a slanted head surface that contacts the seal when the plunger is in the second plunger position.

12. The valve of claim 1 wherein the seal comprises a ball.

13. The valve of claim 1 wherein the biasing member comprises a spring.

14. The valve of claim 1 wherein the housing has a second end opposite the first end of the housing, and wherein the valve further comprises an end cap adjacent the second end of the housing.

15. The valve of claim 1 wherein the housing comprises a front housing removably connected to a back housing, and wherein the front housing forms the first end of the housing.

16. The valve of claim 15 wherein the front housing is permanently connected to the back housing.

17. The valve of claim 15 wherein the front housing is removably connected to the back housing.

18. The valve of claim 15 wherein the back housing comprises a spring seat and the biasing member comprises a spring, the spring adjacent the spring seat and the spring adjacent the plunger.

19. The valve of claim 1 wherein the first end comprises a luer fitting.

20. A self-sealing valve for use in a thoracentesis catheter instrument having a needle extending through a catheter, the valve comprising:
    a housing having a first housing end and an opposite second housing end, the first housing end defining a first opening through the first housing end, the second housing end defining a second opening through the second housing end the housing adapted to have the needle removably extending through the housing and the first and second openings in the first and second housing ends;
    a plunger movable within the housing from a first plunger position to a second plunger position;
    a biasing member adjacent the plunger, wherein the biasing member biases the plunger toward the second plunger position; and,
    a seal positioned within a space between the plunger and the housing, wherein the seal seals the first opening when the plunger is in the second plunger position;
    wherein the seal is not biased toward the first housing end when the plunger is in the first plunger position and the needle extends through the housing, and wherein the seal is biased toward the first, housing end when the plunger is in the second plunger position and the needle is removed from the housing.

21. A plunger adapted for use in a valve having a spring for biasing the plunger into contact with a ball to seal an opening in the valve after a needle, which has an outside diameter, is withdrawn from the valve, the plunger comprising:
   a plunger head adapted to contact the ball when the ball seals the opening; and,
   at least two beams extending from the plunger head, the beams movable from a first position spaced apart from each other toward each other into a second position, wherein the beams in the first position are adapted to engage the valve and hold the plunger against a spring biasing force and wherein the beams in the second position are adapted to disengage the valve to permit the spring to bias the plunger into contact with the ball to seal the opening.

22. The plunger of claim 21 wherein the beams are spaced apart at a first distance in the first position and the beams are spaced apart at a second distance in the second position, the second distance being smaller than the first distance.

23. The plunger of claim 22 wherein the first distance is at least as large as the outside diameter of the needle.

24. The plunger of claim 22 wherein the second distance is smaller than an outside diameter of the needle.

25. The plunger of claim 21 wherein the beams are adapted to permit the needle to extend between the beams when the beams are in the first position.

26. The plunger of claim 21 wherein the beams are adapted to prevent insertion of the needle between the beams when the beams are in the second position.

27. The plunger of claim 21 wherein the plunger head comprises a conical shaped surface adapted to guide the ball towards the opening.

28. The plunger of claim 21 wherein the plunger defines a passageway through the plunger head and between the beams.

29. The plunger of claim 28 wherein the passageway defines a longitudinal axis through the plunger, and the plunger is symmetrical around the axis.

30. The plunger of claim 28 wherein the passageway is adapted to receive the needle when the beams are in the first position.

31. The plunger of claim 28 wherein the beams are adapted to prevent insertion of the needle through the passageway when the beams are in the second position.

* * * * *